United States Patent
Bernard et al.

(10) Patent No.: US 11,051,950 B2
(45) Date of Patent: *Jul. 6, 2021

(54) EXPANSIBLE INTERSOMATIC CAGE

(71) Applicant: LDR Medical, S.A.S., Sainte-Savine (FR)

(72) Inventors: Pierre Bernard, Bordeaux (FR); Herve Chataigner, Boussieres (FR); Craig Chebuhar, Marietta, GA (US); Alexander Kirgis, Krailling (DE); Ross Sherban, Clarence, NY (US); Samuel Lequette, Pessac (FR); Emmanuel Bougere, Bordeaux (FR); Aymeric Fresneau, Bordeaux (FR)

(73) Assignee: LDR Medical, S.A.S., Sainte-Savine (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/453,337

(22) Filed: Jun. 26, 2019

(65) Prior Publication Data
US 2019/0336299 A1    Nov. 7, 2019

Related U.S. Application Data

(63) Continuation of application No. 15/796,735, filed on Oct. 27, 2017, now Pat. No. 10,624,756.

(30) Foreign Application Priority Data

Oct. 27, 2016  (FR) ...................................... 1660473

(51) Int. Cl.
*A61F 2/44* (2006.01)
*A61F 2/30* (2006.01)
*A61F 2/46* (2006.01)

(52) U.S. Cl.
CPC ............ *A61F 2/442* (2013.01); *A61F 2/4455* (2013.01); *A61F 2/30767* (2013.01);
(Continued)

(58) Field of Classification Search
CPC .......... A61F 22/44; A61F 22/442–4425; A61F 22/446–4465; A61F 2002/30537–30545
See application file for complete search history.

(56) References Cited

U.S. PATENT DOCUMENTS 5,059,193 A * 10/1991 Kuslich ................. A61F 2/4455
  606/247
5,171,278 A * 12/1992 Pisharodi ................ A61F 2/446
  128/898

(Continued)

FOREIGN PATENT DOCUMENTS

WO  WO-2015087285 A1  6/2015
WO  WO-2018078148 A1  5/2018

OTHER PUBLICATIONS

"U.S. Appl. No. 14/796,735, Response filed Feb. 13, 2019 to Non Final Office Action dated Nov. 15, 2018", 7 pgs.

(Continued)

*Primary Examiner* — Eduardo C Robert
*Assistant Examiner* — Michelle C Eckman
(74) *Attorney, Agent, or Firm* — Schwegman Lundberg & Woessner, P.A.

(57) ABSTRACT

Various embodiments comprise an expansible intervertebral implant intended to be implanted in a space between two adjacent vertebrae to at least partly supplant an intervertebral disc, said implant being able to expand along three substantially mutually orthogonal axes so as to comply with the lordosis of the patient while still having increased stability and reliability.

20 Claims, 9 Drawing Sheets

(52) U.S. Cl.
CPC ..... *A61F 2/4611* (2013.01); *A61F 2002/3006* (2013.01); *A61F 2002/30112* (2013.01); *A61F 2002/30329* (2013.01); *A61F 2002/30537* (2013.01); *A61F 2002/30538* (2013.01); *A61F 2002/30556* (2013.01)

(56) References Cited

U.S. PATENT DOCUMENTS

| | | | | |
|---|---|---|---|---|
| 5,390,683 | A * | 2/1995 | Pisharodi | A61F 2/446 128/898 |
| 6,723,126 | B1 * | 4/2004 | Berry | A61F 2/4611 623/17.11 |
| 7,731,751 | B2 * | 6/2010 | Butler | A61F 2/446 623/17.11 |
| 7,879,098 | B1 * | 2/2011 | Simmons, Jr. | A61F 2/4465 623/17.11 |
| 8,556,979 | B2 * | 10/2013 | Glerum | A61F 2/447 623/17.16 |
| 9,622,874 | B2 * | 4/2017 | McCormack | A61F 2/4611 |
| 9,795,493 | B1 * | 10/2017 | Bannigan | A61F 2/4455 |
| 9,883,953 | B1 * | 2/2018 | To | A61F 2/442 |
| 9,913,726 | B2 * | 3/2018 | Weiman | A61F 2/442 |
| 10,105,238 | B2 * | 10/2018 | Koch | A61F 2/44 |
| 10,624,756 | B2 | 4/2020 | Bernard et al. | |
| 2005/0113916 | A1 * | 5/2005 | Branch, Jr. | A61F 2/447 623/17.11 |
| 2005/0182417 | A1 * | 8/2005 | Pagano | A61B 17/3472 606/92 |
| 2005/0278028 | A1 * | 12/2005 | Mujwid | A61F 2/446 623/17.13 |
| 2006/0004447 | A1 * | 1/2006 | Mastrorio | A61B 17/7065 623/17.11 |
| 2006/0167547 | A1 * | 7/2006 | Suddaby | A61F 2/446 623/17.11 |
| 2007/0073398 | A1 * | 3/2007 | Fabian | A61F 2/442 623/17.11 |
| 2007/0219634 | A1 * | 9/2007 | Greenhalgh | A61F 2/446 623/17.16 |
| 2007/0233244 | A1 * | 10/2007 | Lopez | A61F 2/4425 623/17.11 |
| 2007/0233261 | A1 * | 10/2007 | Lopez | A61F 2/4425 623/17.13 |
| 2007/0282449 | A1 * | 12/2007 | de Villiers | A61F 2/4611 623/17.15 |
| 2008/0133014 | A1 * | 6/2008 | Gately | A61F 2/4611 623/17.16 |
| 2008/0183204 | A1 * | 7/2008 | Greenhalgh | A61F 2/4611 606/198 |
| 2009/0234389 | A1 * | 9/2009 | Chuang | A61B 17/7065 606/249 |
| 2009/0270873 | A1 * | 10/2009 | Fabian | A61F 2/4425 606/99 |
| 2010/0010633 | A1 * | 1/2010 | Kohm | A61F 2/447 623/17.16 |
| 2010/0016973 | A1 * | 1/2010 | de Villiers | A61F 2/4611 623/17.16 |
| 2010/0069912 | A1 * | 3/2010 | McCormack | A61F 2/4611 606/90 |
| 2010/0161062 | A1 * | 6/2010 | Foley | A61F 2/4611 623/17.16 |
| 2010/0185291 | A1 * | 7/2010 | Jimenez | A61F 2/4611 623/17.16 |
| 2010/0286783 | A1 * | 11/2010 | Lechmann | A61F 2/4455 623/17.12 |
| 2011/0066231 | A1 * | 3/2011 | Cartledge | A61B 17/068 623/2.11 |
| 2011/0276141 | A1 * | 11/2011 | Caratsch | A61F 2/4455 623/17.16 |
| 2012/0004732 | A1 * | 1/2012 | Goel | A61F 2/4425 623/17.16 |
| 2012/0071977 | A1 * | 3/2012 | Oglaza | A61B 17/8858 623/17.11 |
| 2012/0083889 | A1 * | 4/2012 | Purcell | A61F 2/4455 623/17.16 |
| 2012/0123546 | A1 * | 5/2012 | Medina | A61F 2/447 623/17.16 |
| 2012/0215316 | A1 * | 8/2012 | Mohr | A61F 2/442 623/17.16 |
| 2012/0232665 | A1 * | 9/2012 | Godara | A61F 2/4611 623/17.16 |
| 2012/0271422 | A1 * | 10/2012 | Miller | A61F 2/4611 623/17.16 |
| 2013/0012994 | A1 * | 1/2013 | McCormack | A61B 17/1671 606/247 |
| 2013/0110239 | A1 * | 5/2013 | Siegal | A61B 17/7098 623/17.16 |
| 2013/0144388 | A1 * | 6/2013 | Emery | A61B 17/885 623/17.16 |
| 2013/0144391 | A1 * | 6/2013 | Siegal | A61F 2/442 623/17.16 |
| 2013/0166027 | A1 * | 6/2013 | Bellas | A61F 2/447 623/17.16 |
| 2013/0166030 | A1 * | 6/2013 | Biedermann | A61F 2/4611 623/17.16 |
| 2013/0190876 | A1 * | 7/2013 | Drochner | A61F 2/442 623/17.16 |
| 2013/0190877 | A1 * | 7/2013 | Medina | A61F 2/4455 623/17.16 |
| 2013/0197647 | A1 * | 8/2013 | Wolters | A61F 2/446 623/17.16 |
| 2013/0304213 | A1 * | 11/2013 | Aflatoon | A61F 2/4455 623/17.16 |
| 2013/0310939 | A1 * | 11/2013 | Fabian | A61F 2/4455 623/17.16 |
| 2013/0317617 | A1 * | 11/2013 | Mayer | A61F 2/4611 623/17.16 |
| 2014/0012383 | A1 * | 1/2014 | Triplett | A61F 2/4611 623/17.16 |
| 2014/0039622 | A1 * | 2/2014 | Glerum | A61F 2/446 623/17.15 |
| 2014/0100662 | A1 * | 4/2014 | Patterson | A61F 2/4455 623/17.16 |
| 2014/0172106 | A1 * | 6/2014 | To | A61F 2/442 623/17.16 |
| 2014/0188224 | A1 * | 7/2014 | Dmuschewsky | A61F 2/442 623/17.16 |
| 2014/0277471 | A1 * | 9/2014 | Gray | A61F 2/447 623/17.15 |
| 2014/0277481 | A1 * | 9/2014 | Lee | A61F 2/4455 623/17.16 |
| 2015/0012098 | A1 * | 1/2015 | Eastlack | A61F 2/4455 623/17.15 |
| 2015/0018954 | A1 * | 1/2015 | Loebl | A61F 2/4611 623/17.16 |
| 2015/0045893 | A1 * | 2/2015 | Dinville | A61F 2/44 623/17.16 |
| 2015/0073552 | A1 * | 3/2015 | To | A61F 2/4684 623/17.15 |
| 2015/0148908 | A1 * | 5/2015 | Marino | A61F 2/30771 623/17.16 |
| 2015/0173910 | A1 * | 6/2015 | Siegal | A61F 2/4465 623/17.16 |
| 2015/0173913 | A1 * | 6/2015 | Lechmann | A61F 2/446 623/17.16 |
| 2015/0209152 | A1 * | 7/2015 | Patterson | A61F 2/4455 623/17.13 |
| 2015/0230929 | A1 * | 8/2015 | Lorio | A61F 2/447 623/17.16 |
| 2015/0230935 | A1 * | 8/2015 | Aflatoon | A61F 2/447 623/17.16 |
| 2015/0272743 | A1 * | 10/2015 | Jimenez | A61F 2/447 623/17.16 |
| 2015/0282797 | A1 * | 10/2015 | O'Neil | A61F 2/4684 606/279 |
| 2016/0120660 | A1 * | 5/2016 | Melkent | A61F 2/4455 623/17.16 |
| 2016/0166396 | A1 * | 6/2016 | McClintock | A61F 2/30771 623/17.16 |

(56) References Cited

U.S. PATENT DOCUMENTS

| | | | |
|---|---|---|---|
| 2016/0206439 A1* | 7/2016 | To | A61F 2/447 |
| 2016/0278935 A1* | 9/2016 | Overes | A61F 2/442 |
| 2016/0324654 A1* | 11/2016 | Loebl | A61F 2/4425 |
| 2016/0361177 A1* | 12/2016 | Biedermann | A61F 2/4465 |
| 2017/0000622 A1* | 1/2017 | Thommen | A61F 2/447 |
| 2017/0042695 A1* | 2/2017 | Foley | A61F 2/4601 |
| 2017/0056197 A1* | 3/2017 | Weiman | A61F 2/4611 |
| 2017/0105844 A1* | 4/2017 | Kuyler | A61F 2/447 |
| 2017/0119542 A1* | 5/2017 | Logan | A61F 2/442 |
| 2017/0119544 A1* | 5/2017 | Dewey | A61F 2/4425 |
| 2017/0202679 A1* | 7/2017 | Butler | A61F 2/4455 |
| 2017/0216045 A1* | 8/2017 | Dewey | A61F 2/447 |
| 2017/0216051 A1* | 8/2017 | Dewey | A61F 2/4611 |
| 2017/0231778 A1* | 8/2017 | Overes | A61F 2/4465 623/17.16 |
| 2017/0312090 A1* | 11/2017 | Sharabani | A61F 2/44 |
| 2017/0312092 A1* | 11/2017 | Link | A61F 2/4455 |
| 2017/0319352 A1* | 11/2017 | Dewey | A61F 2/4455 |
| 2017/0325967 A1* | 11/2017 | Link | A61F 2/4455 |
| 2017/0340777 A1* | 11/2017 | Ma | A61L 27/50 |
| 2017/0367842 A1* | 12/2017 | Predick | A61F 2/4455 |
| 2017/0367843 A1* | 12/2017 | Eisen | A61F 2/447 |
| 2018/0000606 A1* | 1/2018 | Hessler | A61F 2/447 |
| 2018/0014944 A1* | 1/2018 | Davis | A61F 2/4455 |
| 2018/0078384 A1* | 3/2018 | Suddaby | A61F 2/4611 |
| 2018/0116811 A1* | 5/2018 | Bernard | A61F 2/4455 |
| 2018/0116812 A1* | 5/2018 | Bernard | A61F 2/4455 |
| 2018/0116815 A1* | 5/2018 | Kuyler | A61F 2/28 |
| 2018/0125671 A1* | 5/2018 | Bernard | A61F 2/447 |
| 2018/0185164 A1* | 7/2018 | Sharabani | A61F 2/447 |
| 2018/0193164 A1* | 7/2018 | Shoshtaev | A61F 2/447 |
| 2018/0228617 A1* | 8/2018 | Srour | A61F 2/442 |
| 2018/0311047 A1* | 11/2018 | Liu | A61F 2/4601 |
| 2018/0311048 A1* | 11/2018 | Glerum | A61F 2/4455 |
| 2018/0318101 A1* | 11/2018 | Engstrom | A61F 2/4637 |
| 2019/0029840 A1* | 1/2019 | Sack | A61F 2/4611 |
| 2019/0290448 A1* | 9/2019 | Predick | A61F 2/4611 |
| 2020/0046514 A1* | 2/2020 | Gilbride | A61F 2/442 |

OTHER PUBLICATIONS

"U.S. Appl. No. 15/796,735, Non Final Office Action dated Nov. 15, 2018", 17 pgs.

"U.S. Appl. No. 15/796,735, Notice of Allowance dated Mar. 25, 2019", 5 pgs.

"U.S. Appl. No. 15/796,735, Preliminary Amendment filed Oct. 27, 2017", 6 pgs.

"International Application Serial No. PCT/EP2017/077705, International Search Report dated Feb. 13, 2018", 3 pgs.

"International Application Serial No. PCT/EP2017/077705, Written Opinion dated Feb. 13, 2018", 5 pgs.

"U.S. Appl. No. 15/796,735, Notice of Allowance dated Feb. 26, 2020", 9 pgs.

* cited by examiner

EXPANSIBLE INTERSOMATIC CAGE

CROSS-REFERENCE TO RELATED APPLICATIONS

This application claims priority under 35 U.S.C. § 119 to French Patent Application No. FR1660473 filed in FRANCE on Oct. 27, 2016, which is incorporated herein by reference.

BACKGROUND

The application relates to the field of intervertebral cages and generally to the field of implants intended to be implanted between two adjacent vertebrae to at least partly supplant an intervertebral disc and more particularly, to expansible vertebral implants of the intersomatic cage type.

To remedy to certain pathologies, sometimes it is sought to obtain the fusion of at least two vertebrae, for example when at least one of their adjacent intervertebral discs is lesioned.

From the state of the art, diverse arthrodesis techniques are known, based on diverse types of implants, such as for example intersomatic cages inserted into the place of a disc to promote bone growth arthrodesis and to secure between them two vertebrae.

Such devices are for example illustrated in patent application FR1651637 filed in February 2016, which has intersomatic cages giving the possibility of supplanting an intervertebral disc.

Further, to maximize and enhance the stability and the graft volume contained in such implants, the latter have to cover a volume which approaches as close as possible to the volume occupied by the lesioned vertebral disc. The implants of the prior art therefore generally have a very large volume making their implantation rather invasive for the patient.

A solution, used for reducing the size of the implants during their implantation, was the use of expansible cages such as those described for example in document EP1699389. Such cages, once they are implanted, are deployed by the surgeon to cover a volume approaching the volume of an intervertebral disc and to have a profile giving the possibility of tracking the lordosis of the vertebral column, thereby improving comfort for the patient and stability of the cage.

Nevertheless, this type of expansible cages has a certain number of drawbacks. In particular, during their expansion, the surgeon should exert inordinate pressure on the implant given that its expansion is simultaneously ensured on two axes orthogonal with each other. Further, it is more difficult for the surgeon to observe a specific lordosis. Finally, this type of implant does not rest or only very little on the cortical bone of the vertebra, but on a softer portion of the bone, which reduces its stability and has a risk of sinking therein.

SUMMARY OF THE DISCLOSURE

The object of the present application is therefore to propose an expansible intervertebral implant of the intersomatic cage type, giving the possibility of overcoming at least one part of the drawbacks of the prior art, by proposing an alternative implant having increased stability and reliability, easier expansion for the surgeon while observing lordosis of the patient.

For this purpose, the application relates to an expansible intervertebral implant intended to be implanted in a space between two adjacent vertebrae (V1 and V2) to supplant at least partly an intervertebral disc, characterized in that said implant comprises at least:

an elongated body along an axis (X) comprised between a proximal end and a distal end defined as being the end intended to first penetrate into said intervertebral space,
at least one pivoting arm pivotally mounted with respect to the longitudinal body, between a folded position and a deployed position:
in the folded position, said arm is substantially parallel to the axis (X) and runs along the body,
in the deployed position, said arm is not parallel to the axis (X) and is deployed away from the body and expands said implant along an axis (Y), substantially orthogonal to the axis (X),
means for actuating said arm (21) for deploying it pivot from the folded position to the deployed position.

According to another feature, said at least one pivoting arm may be positioned at the distal end of the elongated body.

According to another feature, said implant may be provided with one or several pairs of pivoting arms, the arms of each of the pairs may be positioned on either side of the elongated body.

According to another feature, said pivoting arms of each pair may be positioned according to axial symmetry, along the axis (X).

According to another feature, said implant may be provided with means for blocking said pivoting arm in its deployed position.

According to another feature, said means for actuating said pivoting arm may be a wedge sliding along an axis substantially parallel or colinear with the axis (X).

According to another feature, said longitudinal body along an axis (X) may comprise at least two sub-portions substantially or at least partially superposed on each other and connected with each other at least in proximity to the proximal end by at least one joint.

According to another feature, each of said sub-portions may include at least one pivoting arm.

According to another feature, said implant may be provided with means for expanding the body along an axis (Z) substantially orthogonal to the axes (X) and (Y).

According to another feature, the means of expanding the body along the axis (Z), may move either one of the distal ends from each other of both sub-portions.

According to another feature, said means for expanding the longitudinal body is may be formed by said means for actuating said at least one pivoting arm.

According to another feature, said means for expanding the longitudinal body may comprise at least one connecting rod which may be locked in a deployed position when said implant is expanded along the axis (Z).

According to another feature, the longitudinal body may be provided with at least one aperture at its proximal end, said aperture being at least configured so as to form at least one passage for:
at least one tool cooperating with:
said means for actuating said at least one pivoting arm, at least from the folded position to the deployed position,
and optionally, said means for expanding the distal end of the longitudinal body along an axis (Z) substantially orthogonal to the axes (X) and (Y),
and/or
at least one anchoring device configured for securing said implant to the adjacent vertebrae (V1 and V2).

It will be noted that the term "substantially" is regularly used in the present description, notably relating to a feature such as an orientation or a direction, so as to indicate that the relevant feature may in fact be slightly different and not be exactly as designated (for example, the expression "substantially perpendicular" should be interpreted as "at least approximately perpendicular" since it may be possible to select an orientation which is not exactly perpendicular to be able to nevertheless fulfill substantially the same function). Further, terms like the term of "substantially" used in the present application may also be interpreted as defining that the technical feature may "in general" ("generally") and often "preferably", as indicated, but that other embodiments or configurations may be within the scope of the present disclosure. Thus, the terms such as "significantly", "substantially" or "approximately" may be omitted in the present application but it will be clear for one skilled in the art that the definitions of the technical features are not limited, even in the absence of such terms.

BRIEF DESCRIPTION OF THE SEVERAL VIEWS OF THE DRAWING

Other features, details and advantages of the object of the application will become apparent upon reading the description which follows with reference to the appended figures, which illustrate.

DETAILED DESCRIPTION OF VARIOUS EMBODIMENTS

Many combinations may be contemplated without departing from the scope of the application; one skilled in the art will select either one depending on economic, ergonomic, dimensional constraints or others which he/she will have to observe.

In addition, a person skilled in the art can possibly make use of the two other applications filed on the same day as the present application, by the same applicant, so as to ascertain possible functional and/or structural features which would be insufficiently detailed or not detailed in the present application. In other words, the entirety of these two other applications (description, claims and figures) can therefore be considered, if need be (depending on the applicable law), as being incorporated in the present application by reference.

More particularly, FIGS. 1A to 1E schematically illustrate the design object of the application, an intervertebral implant as a cage which expands horizontally and vertically so that the initially occupied volume in the intervertebral space is less than the volume occupied in its final position of use. The distribution of the upper and lower contact areas of the implant with the vertebral endplates is then more relevant, i.e, the support on the vertebral endplate's edges and the anterior part are maximised because cortical bone is denser at these locations, and can better carry the load imposed on the vertebrae.

The sets of FIGS. 2A to 2E, 3A to 3D, 4A to 4C, 5A to 6B, 7A to 7D and 8A to 8D illustrate embodiments but non-limiting of the present application. The characteristics of these embodiments may be combined together without any limitation.

The implant 1 comprises an elongated body 2 along an axis X, comprising a proximal end and a distal end. The distal end is the end through which the cage is introduced into the intervertebral space. Said body 2 is provided with at least one arm 21 mounted on a pivot 22, or by any other means known to one skilled in the art, allowing a "pivoting" movement of said arm 21 between a folded position and a deployed position such as a hinge, or a flexible material.

In the folded position, the arm 21 is positioned against the body 2, i.e. it may be substantially parallel to the axis X to minimize the dimensions of the profile of the implant for its implantation in the patient, thereby reducing the invasiveness of the surgical operation.

In the deployed position, i.e. the final position of use, the arm 21 is positioned along an axis Y, so as to be substantially perpendicular to the body 2, and in certain embodiments, said arm 21 may be preferably in abutment against the latter. The deployment of the arm thus allows the implant to occupy a larger space while allowing increased stability and reliability since the surface in contact with the bone of the vertebrae in particular the cortical bone, is greater.

The implant 1 may be provided with an actuation means 3 or 5 for said at least one pivoting arm from the folded position to the deployed position.

According to different embodiments, the triggering of the setting into motion of the arm 21 may be accomplished either by traction or by pressure on behalf of the practitioner. In other embodiments, not shown in the figures, a rotation movement may allow the triggering of the deployment of the arm 21.

Figure 4A:
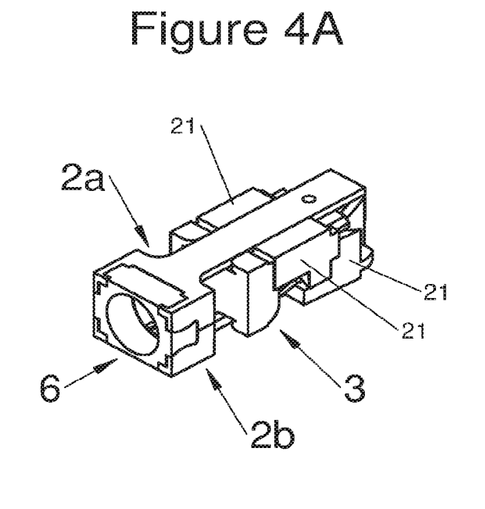
Figure 4B:
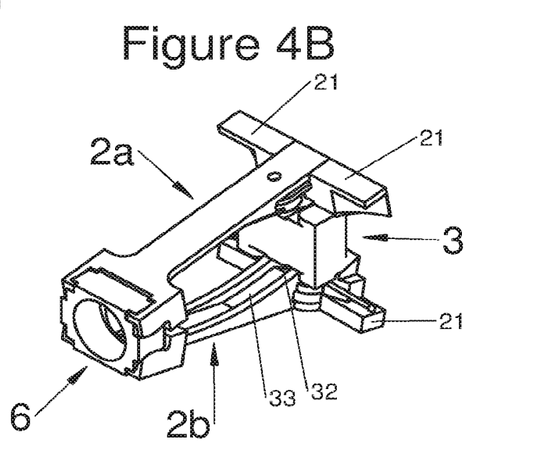
Figure 4C:
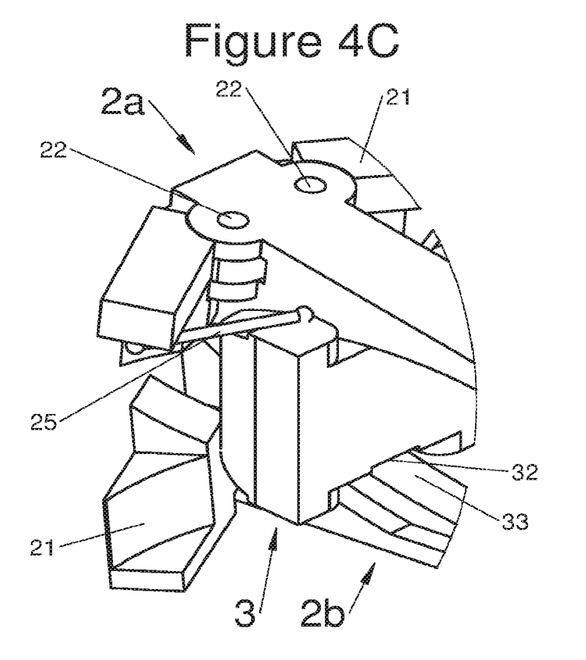
Figure 5A:
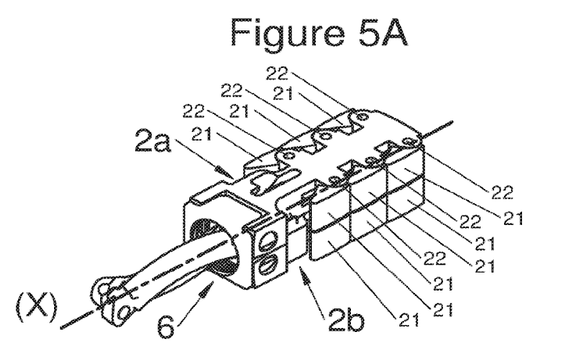
Figure 5B:
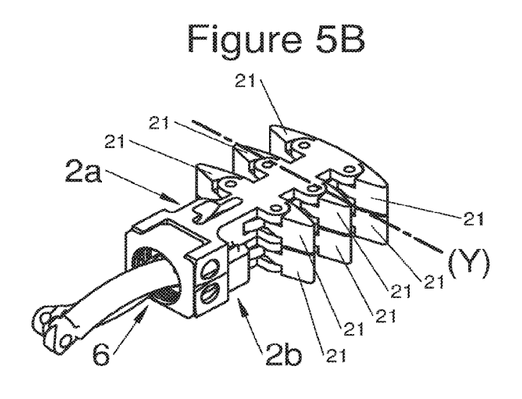
Figure 5C:
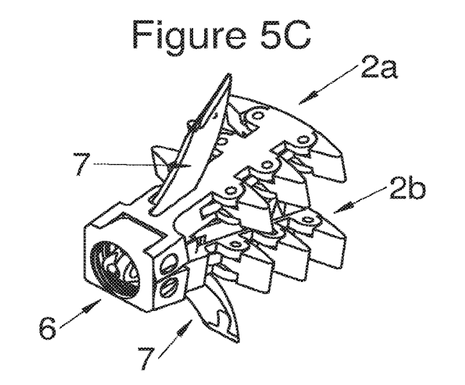
Figure 6A:
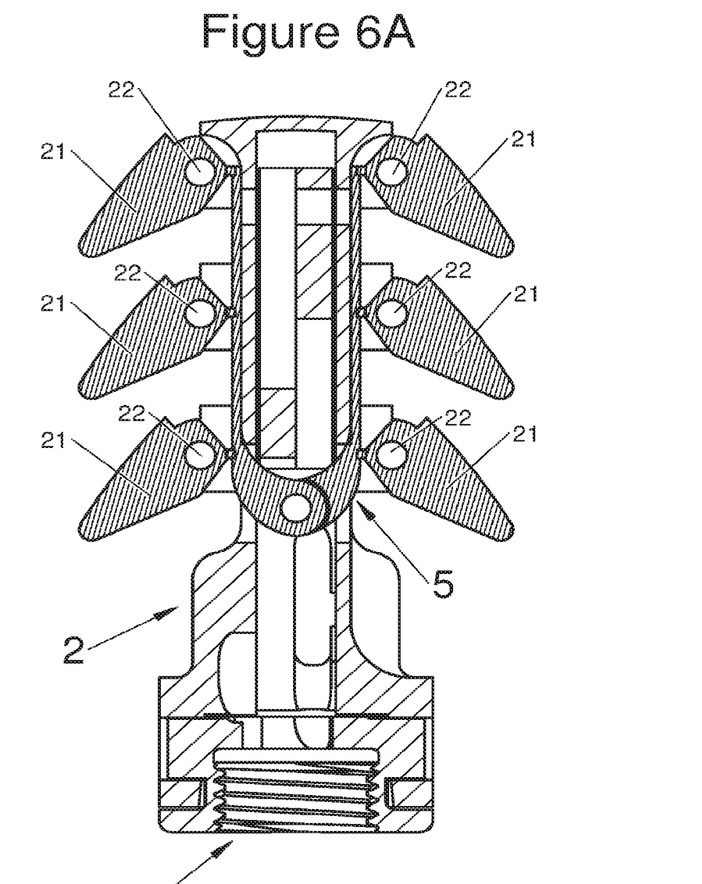
FIGS. 6A to 6B correspond to another embodiment of the present application, with FIG. 6A depicting a sectional view of the sub-portion 2a of FIG. 6B, FIGS. 7A to 7D correspond to another embodiment of the present application.
Figure 6B:
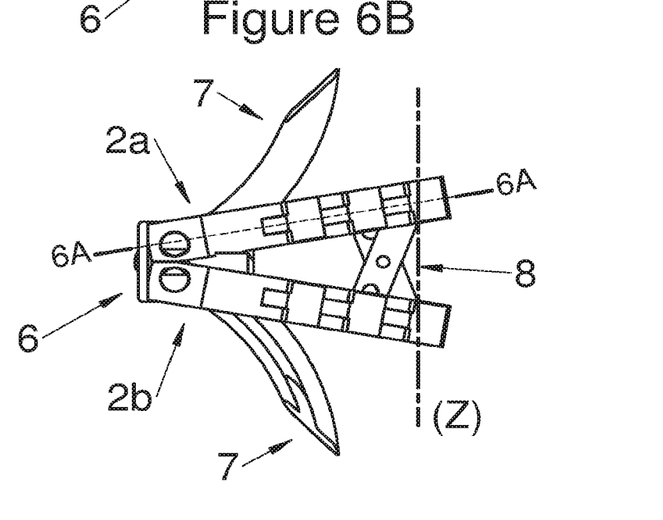
Figure 7A:
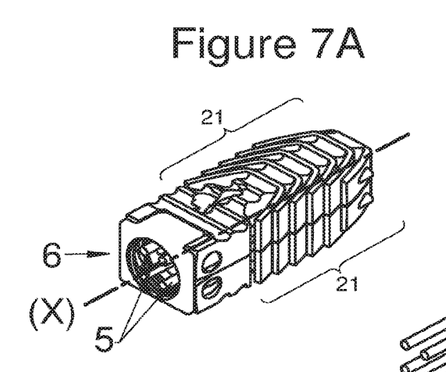
Figure 7B:
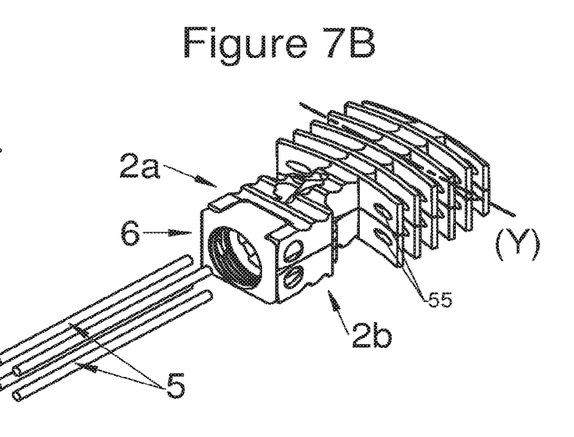
Figure 7C:
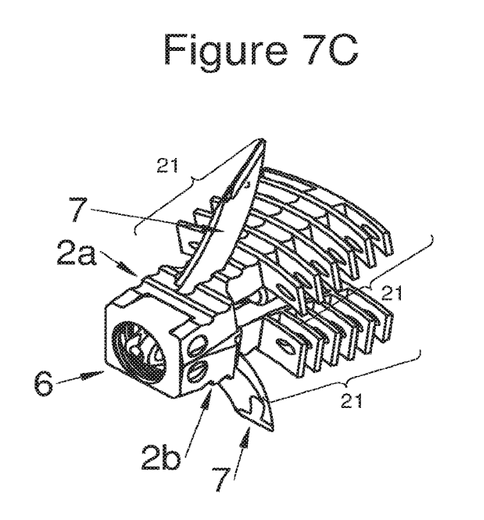
Figure 7D:
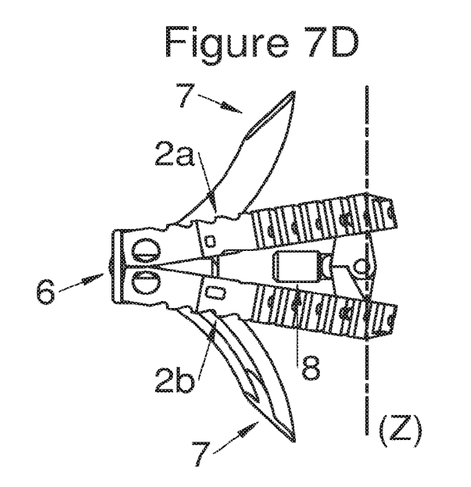

In the case in which pressure is used to deploy the arm, said actuation means may be achieved by means of a wedge 3 which is pushed towards the distal end of the body 2, along a guide 33 having a shape complementary to a portion 32 of the wedge 3. The wedge 3 then will abut against the arm 21 and force the latter to move to assume its deployed position, which may preferably be perpendicular in abutment against the body 2. To facilitate deployment, the wedge 3 and the arm 21 may be connected with each other through a connecting rod 25, thus allowing better transfer of mechanical energy during the deployment of the arm into the final position of use, as shown in FIG. 4C. In certain embodiments, the wedge 3 includes at its distal end 31 a shape complementary to the shape of the arm 21 and allows, by cooperation of shape during the translation of the wedge, to deploy the arm 21 in its deployed position.

Figure 1A:
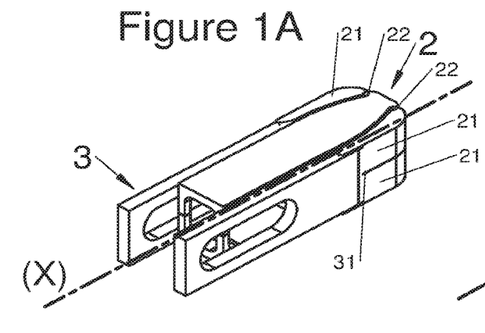
FIGS. 1A to 1E, schematically illustrate an embodiment of the application and its deployment.
Figure 1B:
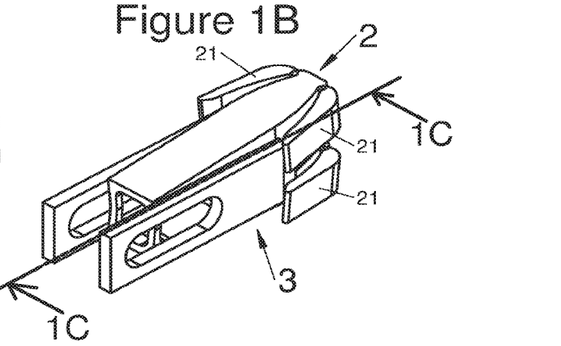
Figure 1C:
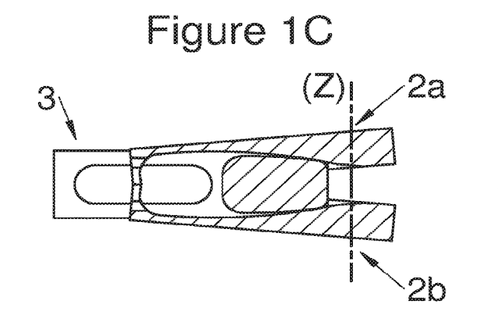
Figure 1D:
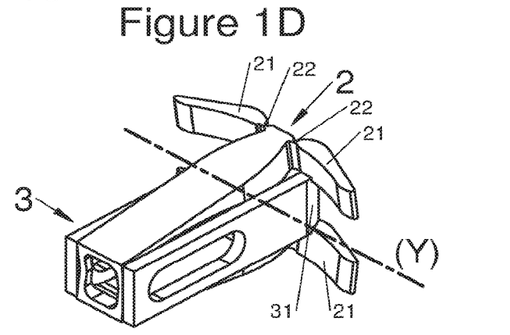
Figure 1E:
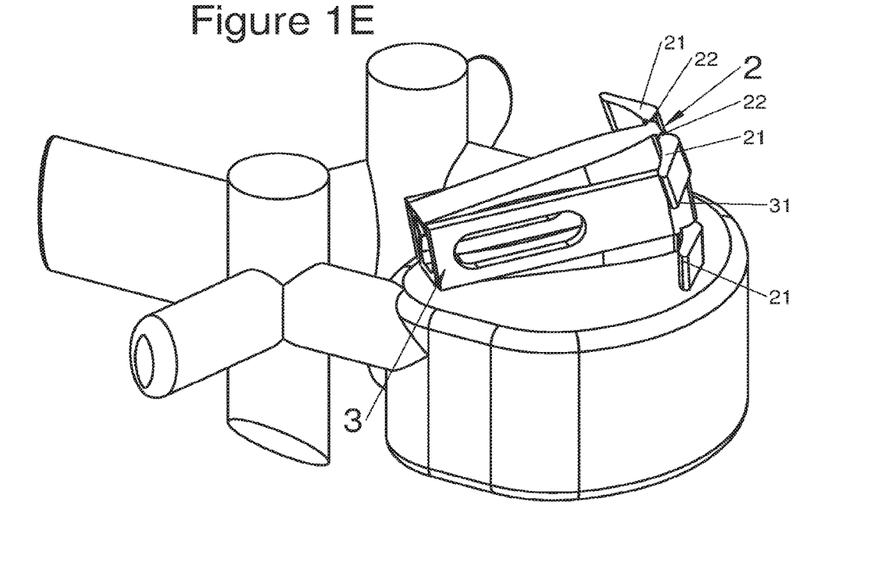
Figure 2A:
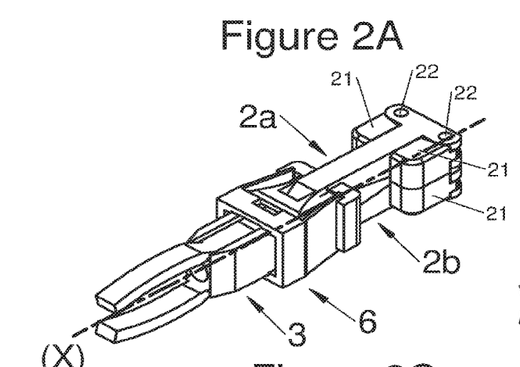
FIGS. 2A to 2E correspond to another embodiment of the present application.
Figure 2B:
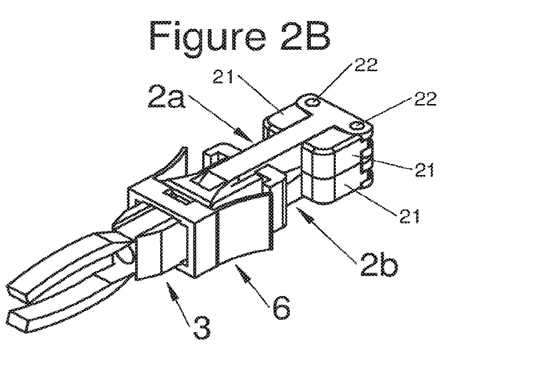
Figure 2C:
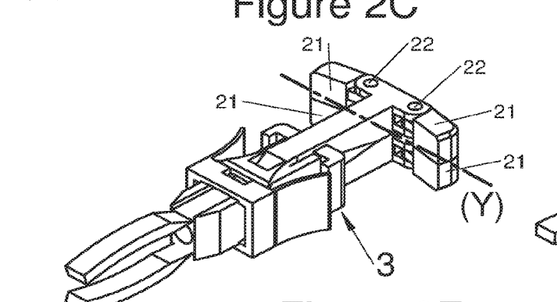
Figure 2D:
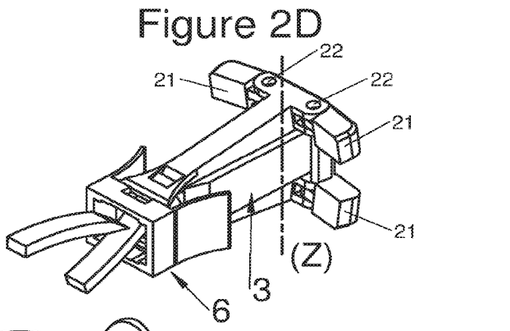
Figure 2E:
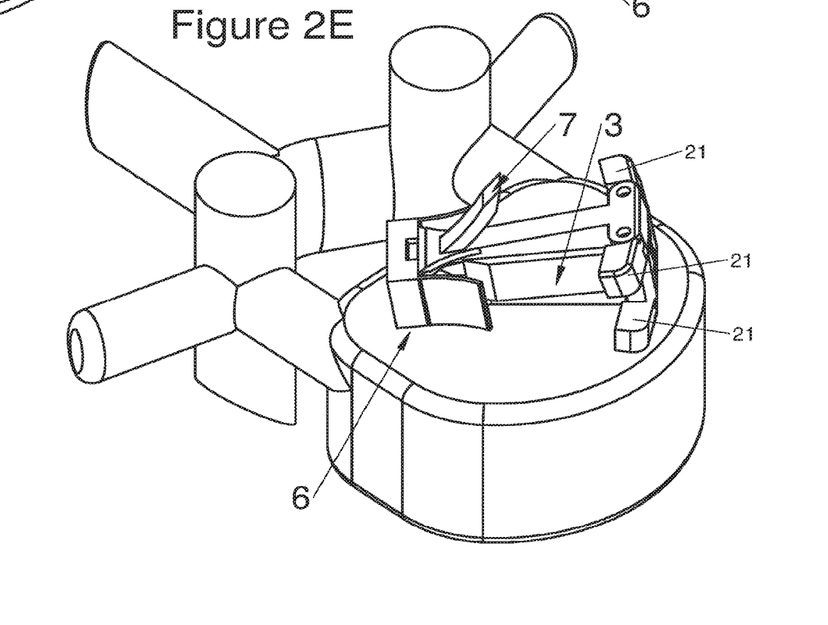
Figures 3A, 3B:
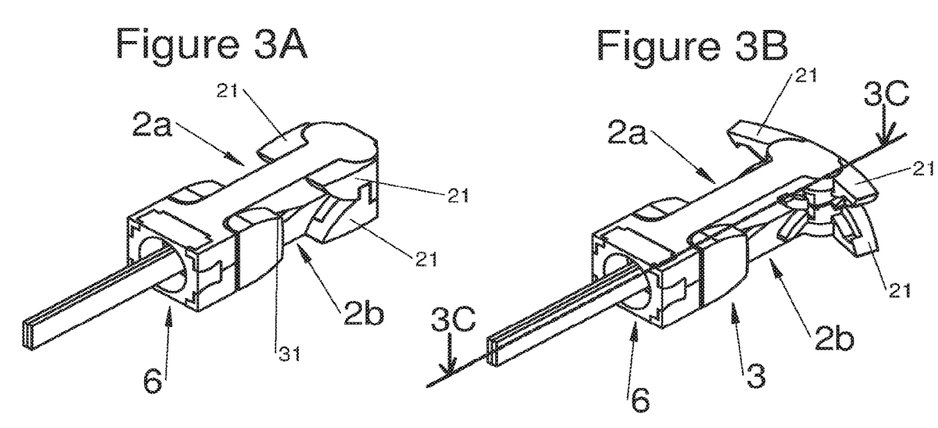
FIGS. 3A to 3D correspond to another embodiment of the present application, with FIG. 3C depicting a sectional view of the distal end of the illustration of the present application illustrated by the set of FIGS. 3A to 3D, FIGS. 4A to 4C correspond to another embodiment of the present application, with FIG. 4C depicting a view of the distal end of the illustration of the present application illustrated by the set of FIGS. 4A to 4C, FIGS. 5A to 5C correspond to another embodiment of the present application.
Figure 3C:
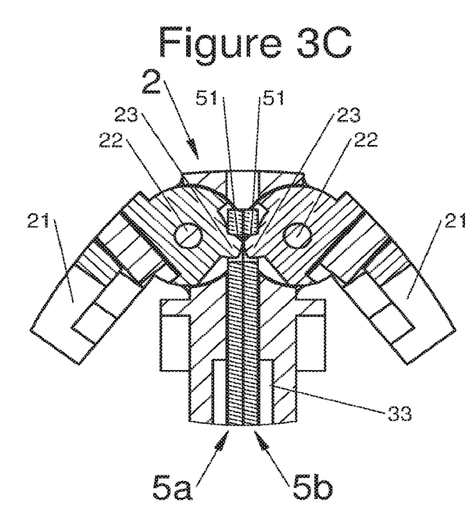
Figure 3D:
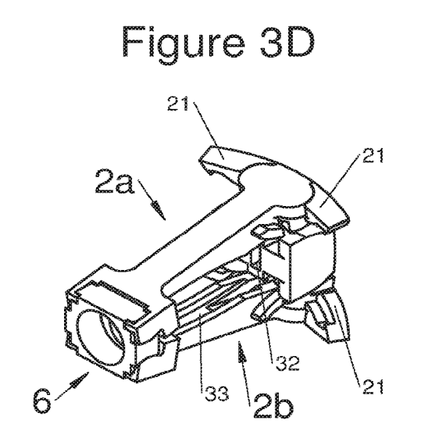

In the case when traction is required for deploying the arm, in certain embodiments as illustrated by FIGS. 3A to 3D, in particular FIG. 3C, a traction part 5, for example as a bar, may be used. The latter may be provided with notches 51 which cooperate with mating notch 23 present on the arm on its edge. When the traction bar 5 carries out a translation towards the proximal end of the body, the notches 51, 23 cooperate together for rotation of the arm around the pivot 22 while releasing the traction bar 5 from the implant 1. To facilitate deployment, the traction bar 5, in certain embodiments, can be formed of two sub-elements 5a and 5b, each of which allows the deployment of one or more distinct arms.

In another embodiment, the traction part 5 may be connected to the arm 21 and uses a pivoting movement to force deployment of the arm into the deployed position, when the traction part is translated towards the proximal end of the implant as illustrated for example in FIGS. 3A to 3D and 6A.

In one embodiment, the arm 21 may consist, at least in part, of a flexible material for example nitinol, which may be subjected to stress in the folded position by at least one traction bar 5. When the practitioner removes the traction bar 5, the arm may be released from the stress allowing the latter to again assume its deployed position as shown for example in FIGS. 7A to 7D. In the no. 7 set of figures, the implant shown comprises several traction bars 5 which pass through an opening 55 of each arm, thus allowing them to be subjected to stress in their folded position.

In various embodiments illustrated by the figures of the present application, said body 2 preferably comprises at least one arm 21 in the vicinity of its distal end, i.e. the end which may be the first in contact with the patient during the implantation of the implant.

According to another embodiment, the implant comprises an even number of arms 21, for example, 2, 4, 6, 8, 10, 12, 14, 16, 18, 20, 22 or further 24 or even more. These pairs can preferably be distributed symmetrically along the body 2 of the implant. However, an embodiment with an odd number of arms 21 is quite possible. In this case, it may be preferable that the arms be positioned alternately on either side of the body 2 of the implant, as in a zigzag.

According to another embodiment, said implant may be provided with a blocking means allowing the pivoting arm to be locked in its deployed position.

According to an embodiment, said longitudinal body may comprise of two sub-portions 2a and 2b positioned on each other. Both sub-portions are connected together through at least one joint 6. Preferably, this joint is found at the proximal end of the body, i.e. on the side closest to the vertebral spines when said implant is implanted in a patient, in other words on the side of the implant opposite to that of the implantation.

Said joint 6 allows a movement of both sub-portions 2a and 2b and in particular of their respective distal ends along an axis Z substantially orthogonal to the axes X and Y.

In an embodiment, said joint 6 may be provided with fins which deploy according to a movement along the axis Y, during the setting into motion of the wedge 3. Such a deployment, illustrated by FIGS. 2A to 2E, gives the possibility of enlarging the volume occupied by the implant in the intervertebral space and promotes the stability of the latter. Moreover, these fins also may help better contain the graft and prevent it from migrating into contact with the roots or the dura mater.

According to another embodiment, the implant 1 has means 3 for expanding the longitudinal body along an axis Z orthogonal to the axes X and Y. In particular said expansion means 3 or 8 allows the distal ends of the sub-portions 2a and 2b to move away from each other. Such a feature allows observance of the lordosis of the vertebral column. Further, the expansion along the axis Z may be modulated by the surgeon during the implantation so as to perfectly correspond to lordosis of the patient.

To do this, the expansion means may, according to the embodiments, be:
  as a connecting rod 8 having at least one locking position,
  as a wedge. This wedge 3 which may coincide with the wedge of the means for actuating the arms on a pivot. Said wedge according to the embodiments slides along the body 2 in at least one guide 33 having a shape mating a portion 32 of the wedge.

Further, when the implant expands along the axes Y and Z, the expansions may be:
  sequential, a first expansion along the axis Y, and then a second expansion along the axis Z or further a first expansion along the axis Z, and then a second expansion along the axis Y, or
  simultaneous, i.e. the expansion along the axis Y being concurrent with the expansion along the axis Z.

Nevertheless, without being limiting, a sequential expansion beginning with the Y axis may be preferred. Indeed, due to the stresses on the vertebrae and on the vertebral column generally, it may be easier to perform expansion along the axis Y than expansion along the axis Z.

Figures 8A, 8B:
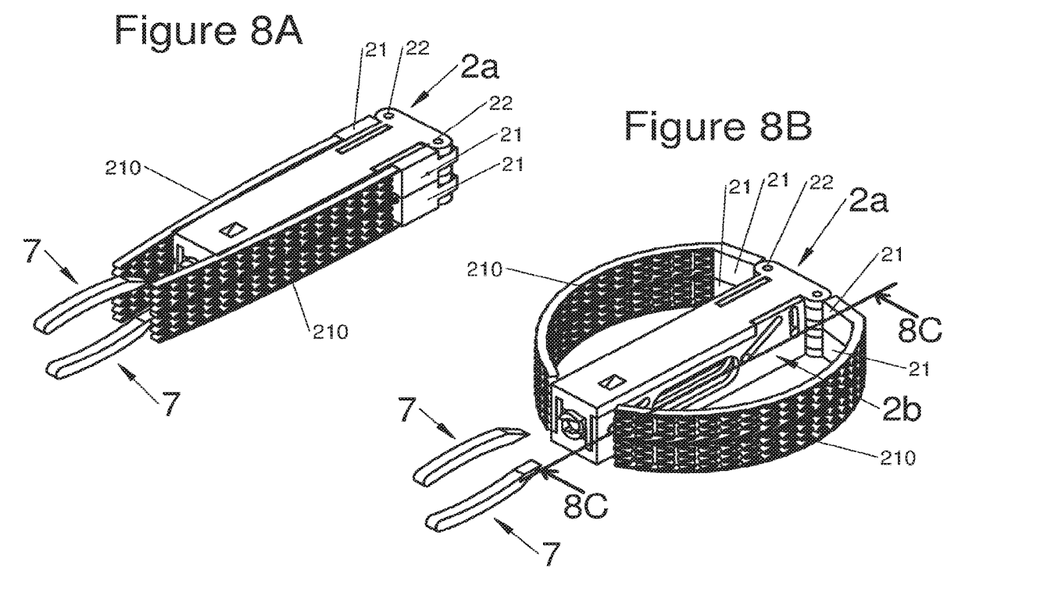
FIGS. 8A to 8D correspond to another embodiment of the present application, with FIG. 8C depicting a profile view of the illustration of the present application illustrated by the set of FIGS. 8A to 8D, without the extensions of the arms 210.
Figure 8C:
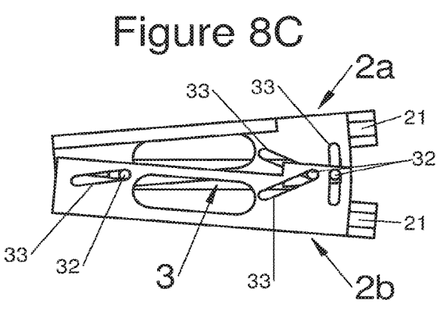
Figure 8D:
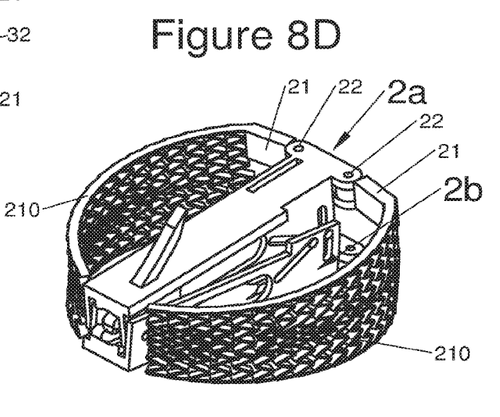
Figures 9A, 9B, 9C, 9D:
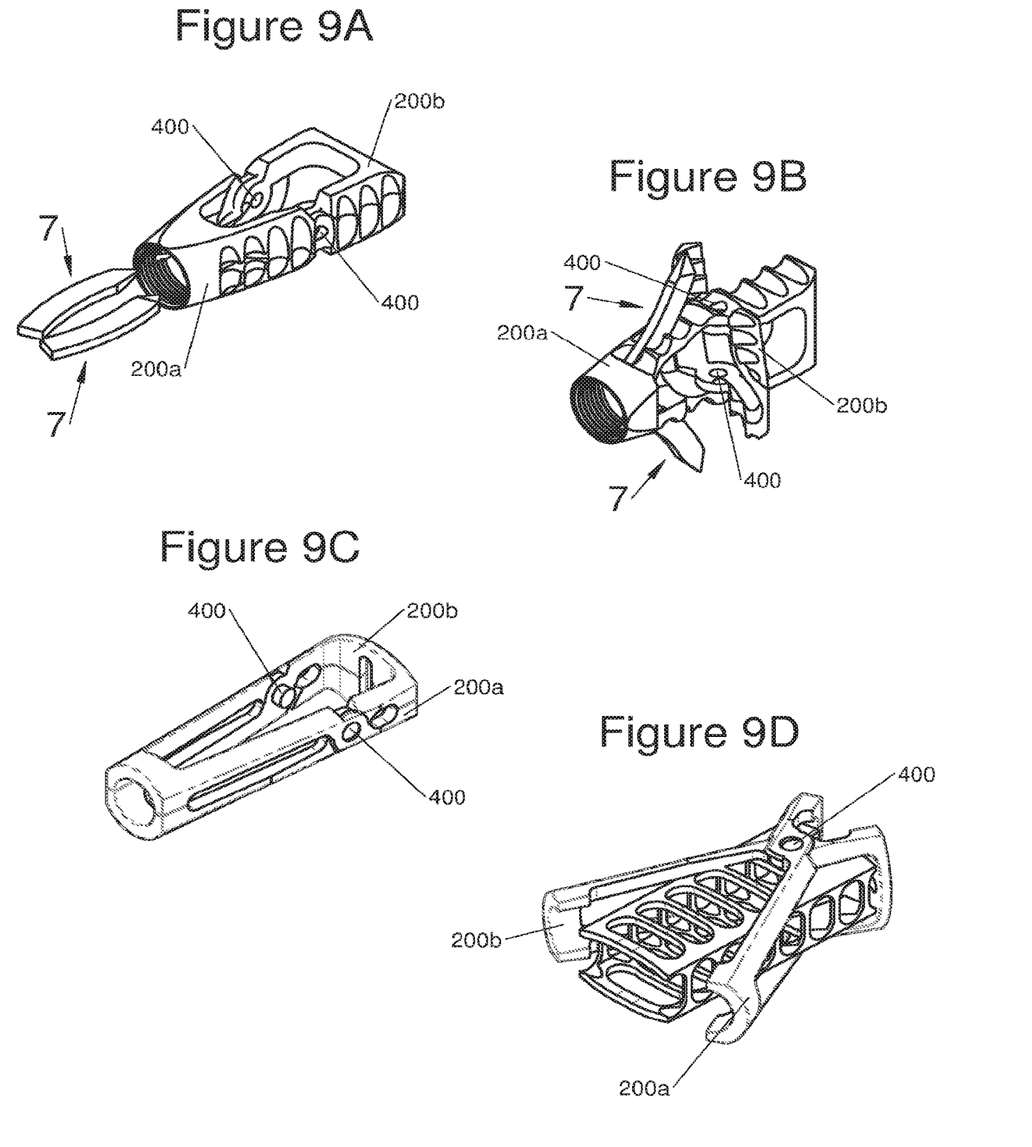
FIGS. 9A to 9D correspond to another embodiment of the present application.

The pivoting arm 21 may be provided with flexible extensions 210 as illustrated by the set of FIGS. 8A to 8D to increase the final volume occupied by the implant in the intervertebral space. Such extensions may be for example made in nitinol. Further their free ends may be hooked-up to or placed in proximity to the proximal end of the implant to "circularize" the pivoting arms as shown in FIGS. 8B and 8D. Preferentially, such extensions comprise a structure allowing its extension along an axis collinear with the axis Z, for example a meshing compressed beforehand, as illustrated in FIG. 8D. Thus, with such structures, the compressional forces which are experienced by the implant, are distributed over the whole of the latter, enhancing its stability. These flexible extensions also allow closure of the graft area of the implant and containment of the graft that will subsequently be injected into the implant.

Said longitudinal body may be provided with an aperture at its proximal end, to let through a tool actuating said actuation means for said at least one pivoting arm from the folded position to the deployed position, and/or, said means for expansion of the distal end of the longitudinal body along an axis Z orthogonal to the axes X and Y, and/or letting through at least one anchor or anchoring device 7 configured so as to secure said cage to the adjacent vertebrae (V1 and V2). Furthermore, the opening allows the introduction of a graft to promote bone growth and thus enhance the stability of the implant.

FIGS. 9A to 9D illustrate alternative embodiments which comprise an elongated body comprising two sub-portions 200a and 200b mounted on a pivot 400 and able to pivot like scissors. A wedge may be inserted as perfectly illustrated in FIG. 9D to secure the deployment of the cage.

In certain embodiments, the implants may be preferably provided with apertures. These apertures may be on either side to promote bone growth within them. These apertures thus allow reinforcement of the anchoring and of the stability of the implant.

It will easily be understood upon reading the present application that the particularities of the present application, as generally described and illustrated in the figures, may be arranged and designed according to a great variety of different configurations. Thus, the description of the present application and the relating figures are not provided for limiting the scope of the application but simply illustrate selected embodiments.

One skilled in the art will understand that the technical features of a given embodiment may in fact be combined with characteristics of another embodiment unless the opposite is explicitly mentioned or unless it is obvious that these characteristics are incompatible. Further, the technical features described in a given embodiment may be isolated from the other features of that embodiment unless the opposite is explicitly mentioned. In particular, the embodiments described in the present application, although they are detailed with reference to illustrative and non-limiting figures, in which the implant may be designed for a posterior approach implantation, are not limited to a particular vertebral level or to a particular implantation route. It is therefore clear that these features could be adapted to a thoracic, cervical, or lumbar implantation, and by the different routes of traditional approaches (anterior, posterior, lateral etc.). The arrangement of the various components of the implant may then be modified to allow such an implantation, and so that the expansion of the implant is suited to its position in the spine and complying with the configuration of the latter. For example, in the case of an implantation by an anterior route, it is easily possible to consider having a gripping means of the implant allowing said implant to be held at its distal end (i.e. the end opposite to the joint 6), and allowing the movement of the actuation means, preferably thanks to a traction, to expand the cage in one or two dimensions.

It should be obvious for those skilled in the art that the present application allows embodiments under many other specific forms without departing from the field defined by the scope of the appended claims, they should be considered as an illustration and the application should not be limited to the details given above.

The invention claimed is:

1. An expandable interbody implant comprising:
    a body elongated along a first axis extending between a proximal end and a distal end of the body;
    a first pair of opposing arms pivotally mounted to the distal end of the body, the first pair of opposing arms pivotable from a folded position to a deployed position, each arm of the first pair of opposing arms including a flexible extension extending from a free end of each arm; and
    an actuation means configured to transition the first pair of opposing arms from the folded position to the deployed position to laterally expand the interbody implant, wherein the body includes an upper portion hinged with a lower portion, and the actuation means includes a wedge device to separate distal ends of the upper portion and the lower portion in the deployed position.

2. The expandable interbody implant of claim 1, wherein the flexible extension extending from the free end of each arm forms an arcuate lateral extension of the interbody implant in the deployed position.

3. The expandable interbody implant of claim 2, wherein the body includes an aperture in the proximal end to deliver bone graft material into space created along lateral sides of the body by the flexible extension extending from the free end of each arm of the pair of opposing arms in the deployed position.

4. The expandable interbody implant of claim 2, wherein the flexible extension extending from the free end of each arm includes an expandable mesh material.

5. The expandable interbody implant of claim 2, wherein the flexible extension extending from the free end of each arm is formed out of nitinol.

6. The expandable interbody implant of claim 1, wherein the body includes an aperture in the proximal end comprising a channel extending through a superior surface of the body and adapted to receive a bone anchor device.

7. The expandable interbody implant of claim 1, wherein the first pair of opposing arms pivot on opposing edges of a distal end of the upper portion; and wherein the lower portion includes a second pair of opposing arms pivotably coupled to opposing edges of a distal end of the lower portion.

8. The expandable interbody implant of claim 7, wherein each arm of the second pair of opposing arms includes a flexible extension extending from a free end of each arm.

9. The expandable interbody implant of claim 8, wherein the flexible extensions extending from the free ends of the first pair of opposing arms and the second pair of opposing arms include an expandable mesh body facilitating expansion of the flexible extensions in a superior-inferior direction in the deployed position.

10. The expandable interbody implant of claim 1, wherein each of the upper portion and the lower portion include angled slots along lateral sides to receive portions of the actuation means.

11. An expandable interbody implant comprising:
    a body elongated along an X-axis extending between a proximal end and a distal end of the body, the body including a superior portion movably coupled to an inferior portion;
    a plurality of arms including a first arm, a second arm, a third arm and a fourth arm, the first arm pivotably coupled to a lateral distal portion of the superior portion of the body, the second arm pivotably coupled to the superior portion opposite the first arm, the third arm pivotably coupled to a lateral distal portion of the inferior portion of the body, and the fourth arm pivotably coupled to the inferior portion opposite the third arm;
    a plurality of flexible extensions extending from free ends of each arm of the plurality of arms; and
    an actuation means configured to transition the plurality of arms from a delivery position folded against lateral sides of the body to a deployed position pivoted laterally outward to expand the interbody implant along a Y-axis.

12. The expandable interbody implant of claim 11, wherein each flexible extension of the plurality of flexible extensions form a semi-circular lateral extension of the interbody implant in the deployed position.

13. The expandable interbody implant of claim 12, wherein each flexible extension of the plurality of flexible extensions form the semi-circular lateral extension by arching from the free ends of the plurality of arms proximally to the proximal end of the body.

14. The expandable interbody implant of claim 11, wherein the body includes an aperture in the proximal end to deliver bone graft material into space created by the plurality of flexible extensions extending from the free ends of the plurality of arms.

15. The expandable interbody implant of claim 11, wherein the body includes an aperture in the proximal end comprising a channel extending through a superior surface of the superior portion of the body and adapted to receive a bone anchor device.

16. The expandable interbody implant of claim 11, wherein the plurality of flexible extensions extending from the free ends of the plurality of arms include an expandable mesh body facilitating expansion of the flexible extensions in a Z-axis in the deployed position.

17. The expandable interbody implant of claim 11, wherein the actuation means includes a wedge structure translatable between the superior portion and the inferior portion to expand the body along a Z-axis.

18. The expandable interbody implant of claim 11, wherein each of the superior portion and the inferior portion include angled slots along lateral sides to receive complementary portions of the actuation means.

19. The expandable interbody implant of claim 18, wherein linear translation of the actuation means causes the complementary portions to slide along the angled slots to expand the expandable interbody implant along the Z-axis.

20. An expandable interbody implant comprising:
a body elongated along a first axis extending between a proximal end and a distal end of the body;
a first pair of opposing arms pivotally mounted to the distal end of the body, the first pair of opposing arms pivotable from a folded position to a deployed position, each arm of the first pair of opposing arms including a flexible extension extending from a free end of each arm; and
an actuation means configured to transition the first pair of opposing arms from the folded position to the deployed position to laterally expand the interbody implant,
wherein the body includes an aperture in the proximal end comprising a channel extending through a superior surface of the body and adapted to receive a bone anchor device.

* * * * *